United States Patent [19]

Matasovic

[11] Patent Number: 5,525,216
[45] Date of Patent: Jun. 11, 1996

[54] FLOATING INLET TUBE

[75] Inventor: Jozef D. Matasovic, Salt Lake City, Utah

[73] Assignee: Baker Hughes Incorporated, Houston, Tex.

[21] Appl. No.: 305,150

[22] Filed: Sep. 13, 1994

Related U.S. Application Data

[62] Division of Ser. No. 207,753, Mar. 8, 1994, Pat. No. 5,384,033.

[51] Int. Cl.$^6$ ..................................... C02F 3/28
[52] U.S. Cl. .................. 210/121; 210/219; 210/DIG. 9; 210/242.1; 366/279
[58] Field of Search ..................................... 210/121, 122, 210/218, 219, 242.1, 242.3, 603, DIG. 9; 366/279, 318

[56] References Cited

U.S. PATENT DOCUMENTS

| | | | |
|---|---|---|---|
| 3,255,887 | 6/1966 | Walker et al. | 210/DIG. 9 |
| 3,288,295 | 11/1966 | Kelly | 210/121 |
| 4,094,338 | 6/1978 | Bauer | 210/242.1 |
| 4,349,355 | 9/1982 | Lingappa et al. | 210/DIG. 9 |
| 4,575,256 | 3/1986 | Armitage et al. | 366/266 |
| 4,581,181 | 4/1986 | Nicholls | 210/242.1 |
| 4,695,376 | 9/1987 | Astrom et al. | 210/242.1 |
| 4,781,827 | 11/1988 | Shields | 210/242.1 |
| 4,956,100 | 9/1990 | Mikkleson | 210/122 |
| 4,998,585 | 3/1991 | Newcomer et al. | 210/242.3 |
| 5,104,528 | 4/1992 | Christie | 210/242.1 |

*Primary Examiner*—Christopher Upton
*Attorney, Agent, or Firm*—Trask, Britt & Rossa

[57] ABSTRACT

A floating inlet assembly for use with a mixing apparatus in a digester. The floating inlet assembly comprising a floating inlet housing which is vertically reciprocable with respect either to a fixed inlet tube or to a guide tube structure.

10 Claims, 6 Drawing Sheets

FLOATING INLET TUBE

This is a division of application Ser. No. 08/207,753, filed Mar. 8, 1994, now U.S. Pat. No. 5,384,033.

BACKGROUND OF THE INVENTION

1. Field of the Invention

The invention relates to an improved mixing device for use in biological actor apparatus. More specifically, this invention relates to an improved float tube assembly for a sludge mixing apparatus for use in digesting apparatus for treating municipal waste sludge and the like.

Typically, digesting apparatus for treating municipal sludge waste comprises a tank having an inlet and outlet and a floating or fixed cover or dome. Gas evolving material, commonly referred to as sludge, to be anaerobically digested is admitted through the sludge feed pipe (inlet) to the digester, while supernant or treated material is withdrawn through the outlet located at the desired surface level of the liquid.

2. State of the Art

During the anaerobic digestion of the sludge gas evolves and is trapped under the cover of the digester. Since the rate of gas production varies it is desirable to use floating ballast type covers for the digester. Such covers are shown in U.S. Pat. Nos. 3,535,236, 4,378,437 and 4,391,705.

To enhance the rate of the digestion of the organic material in the sludge, it is desirable to mix the contents of the digester. Typical prior art mixing apparatus for use in digesters are shown in U.S. Pat. Nos. 4,422,771, 4,575,256 and 4,997,557. To promote efficient mixing of the sludge in the digester it is preferred that the liquid, scum, and any foam thereon be continuously mixed into the materials in the lower part of the digester. Since the fluid level in the digester can vary as well as the amount of free liquid, scum and any foam thereon, even though the digester may include a floating cover, accurate vertical placement of the mixing apparatus within the digester is difficult to ensure so that at any point in time the mixing apparatus inlet will have access to free liquid, scum and any foam thereon for mixing into the material therebelow. If the mixing apparatus does not have access to liquid to mix into the sludge, little beneficial mixing of the sludge can take place. It is also desirable that the mixing apparatus have access to any scum and foam on the surface of the liquid in the digester so that the mixing apparatus can break down the scum and foam.

Various types of floating inlet and skimming apparatus for digesters are illustrated in U.S. Pat. Nos. 3,303,932, 4,094,338, 4,153,071, 4,024,062 and 4,956,100. Other types of skimming apparatus are illustrated in U.S. Pat. Nos. 3,633,749, 4,663,037, 4,761,225, 4,626,358 and 4,998,585.

BRIEF SUMMARY OF THE INVENTION

The present invention is directed to a floating inlet assembly for a mixing apparatus for use in a digester or biological reactor apparatus. The present invention of a floating inlet assembly may comprise several arrangements depending upon the location of the mixing apparatus with respect to the digester or biological reactor apparatus. The floating inlet assembly for a mixing apparatus comprises a floating inlet housing which is vertically reciprocable with respect either to a fixed inlet tube or to a guide tube structure.

The present invention will be better understood when the drawings are taken in conjunction with the detailed description of the invention hereafter.

DETAILED DESCRIPTION OF THE INVENTION

Figure 1:
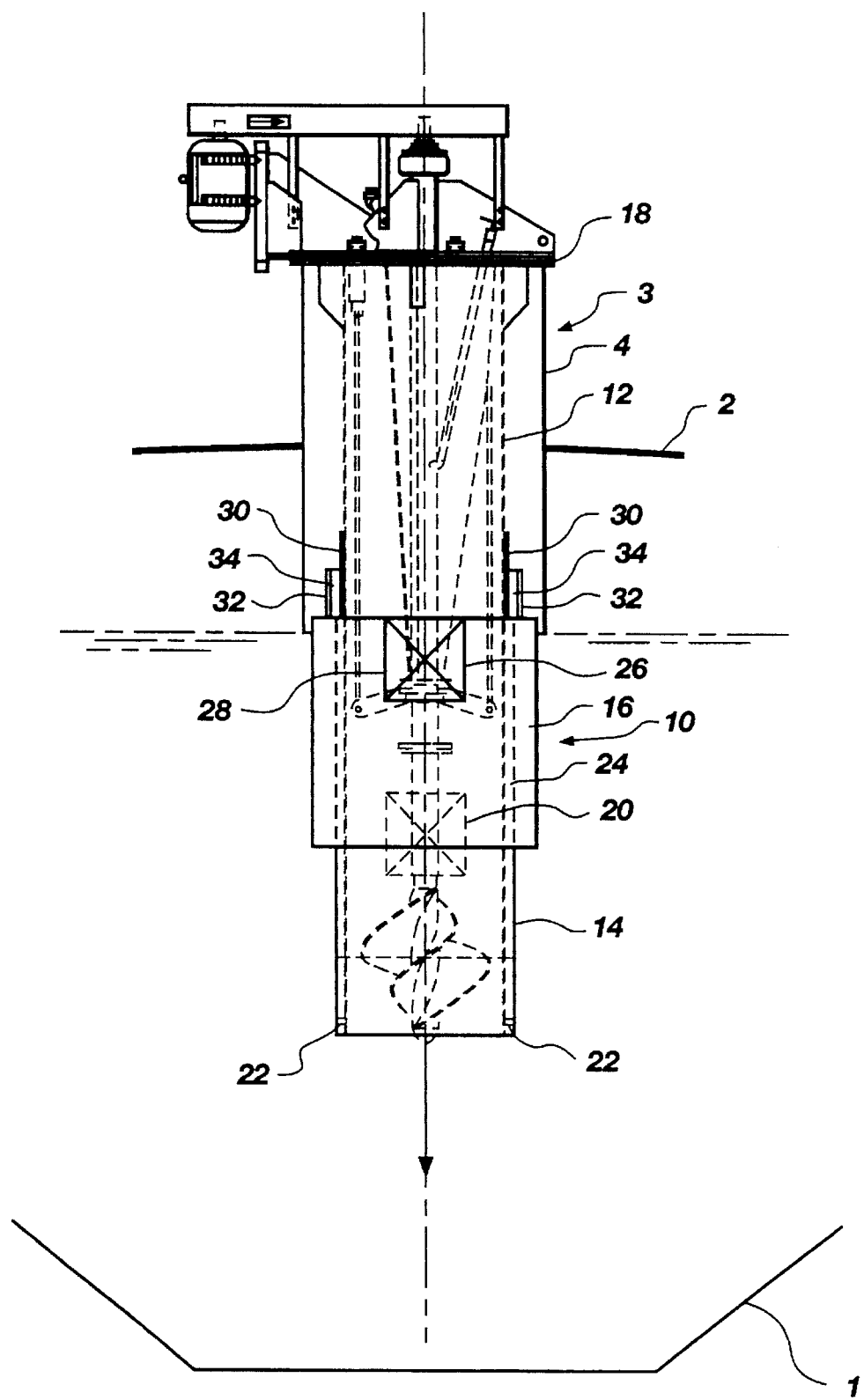
FIG. 1 is a side view of an embodiment of the present invention in a digester at its upper liquid level.

Referring to drawing FIG. 1, a fast embodiment 10 of the float tube assembly of the present invention is shown.

The float tube assembly 10 of the present invention is shown in a digester 1 having a floating cover 2 and mixing apparatus 3 installed therethrough. The mixing apparatus 3 may be of any suitable configuration such as illustrated in U.S. Pat. No. 4,575,256 which is incorporated herein by reference.

The float tube assembly 10 of the present invention comprises fixed inner housing 12, floating housing 14 and annular float 16.

The fixed inner housing 12 comprises an elongated annular cylindrical member extending through pump assembly housing 4 and secured to a portion of the mixing apparatus 3 at the upper end 18 of the fixed inner housing 12. The fixed inner housing 12 contains one or more apertures 20 therein which may be of any desired shape to allow fluid flow therethrough. The length of the fixed inner housing 12 may be any desired length depending upon the size of the digester 1 and the fluids levels therein. Contained on the exterior of inner housing 12 near the lower end thereof is seal 22. The seal 22 may be of any suitable type, such as a scraper-type seal, but need not be a fluid tight seal. The seal 22 need be a sufficient type seal to prevent debris, solids, and liquid from substantially entering the annular space 24 between faced inner housing 12 and floating housing 14.

The floating housing 14 comprises an elongated annular cylindrical member having one or more apertures 26 through the upper end thereof, The length of the floating housing 14 may be any desired length depending upon the size of the digester 1 and the fluid levels therein so long as there is sufficient overlap of the fixed inner housing 12 and floating housing 14 to prevent disengagement therebetween. The apertures 26 may be of any suitable size and shape to allow the flow therethrough of liquid, scum and/or foam from the digester 1.

The annular float 16 comprises an elongated annular cylindrical member secured to the upper end of floating housing 14 by any suitable means, such as welding. The annular float 16 contains one or more apertures 28 therein which allow communication with apertures 26 of the floating housing 14. The annular float 16 may be of any suitable length so long as the annular float 16 has sufficient buoyant capacity to float in the anticipated liquid and particulate material in the digester 1 and cause the floatation of the floating housing 14. The annular float 16 may be formed in any suitable manner, such as an annular chamber filled with closed cell foamed material, employing a ballast chamber, employing separate ballast chambers, pontoons, etc.

Attached to the exterior of fixed inner housing 12 is a plurality of elongated arcuate plates 30. Secured to the upper end of floating housing 14 and/or annular float 16 is a plurality of arms 32 or guides having rub blocks 34 secured thereto to rub on plates 30 to guide floating housing 14 with respect to fixed inner housing 12.

As shown in drawing FIG. 1, the floating housing 14 having annular float 16 secured thereto is in its upper most position with respect to the fixed housing 12.

Figure 2:
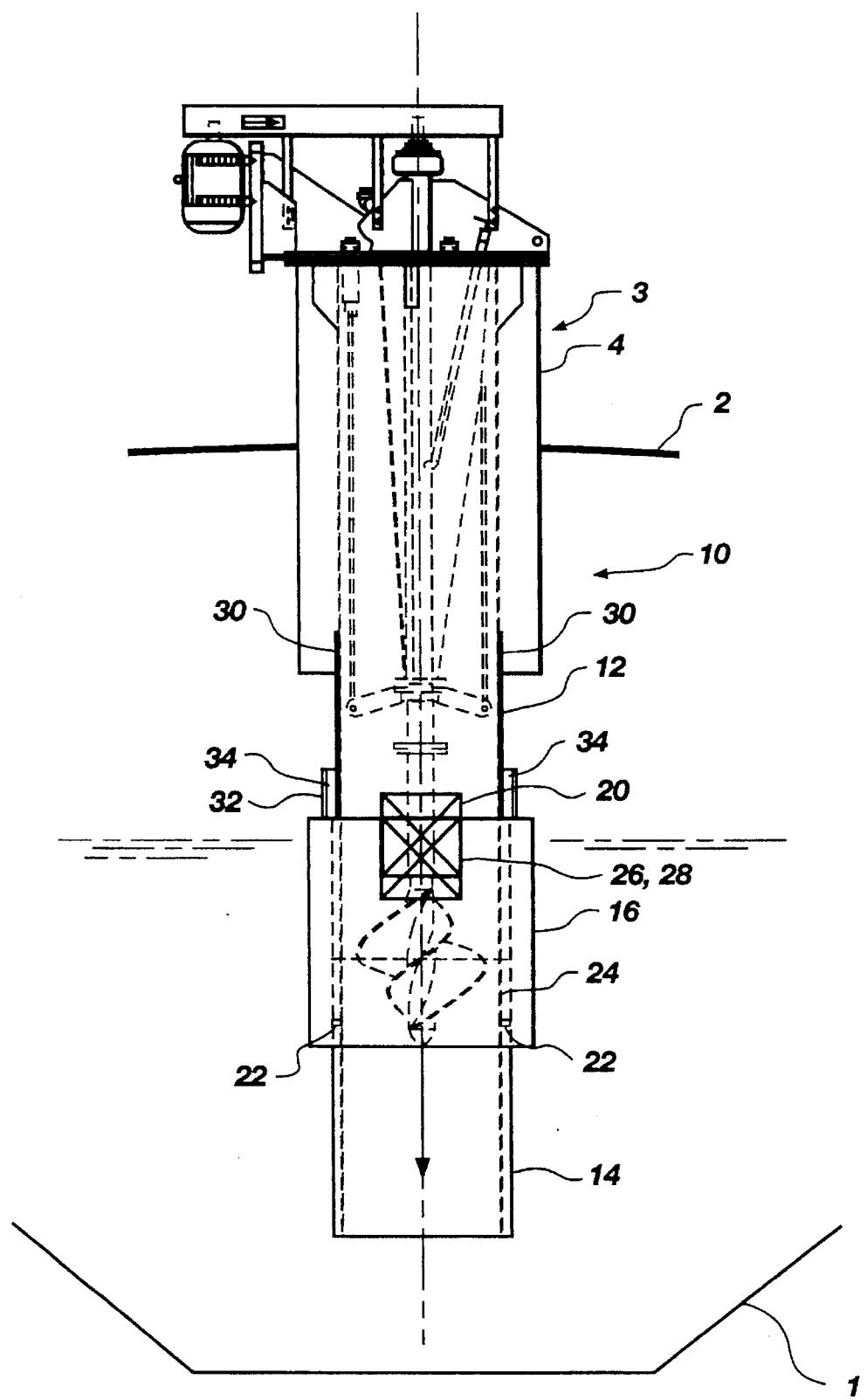
FIG. 2 is a side view of the embodiment of the present invention of FIG. 1 in a digester at its lower liquid level.

Referring to drawing FIG. 2, the floating housing 14 having float 16 secured thereto is shown in its lowest position with respect to the fixed housing 12. In this position, the apertures 26, 28' in float housing 14 and annular float 16 respectively are in close fluid communication. The annular seal 22 maintains the substantial sealing of the annular space 24 between fixed housing 12 and float housing 14.

Figures 3, 4:
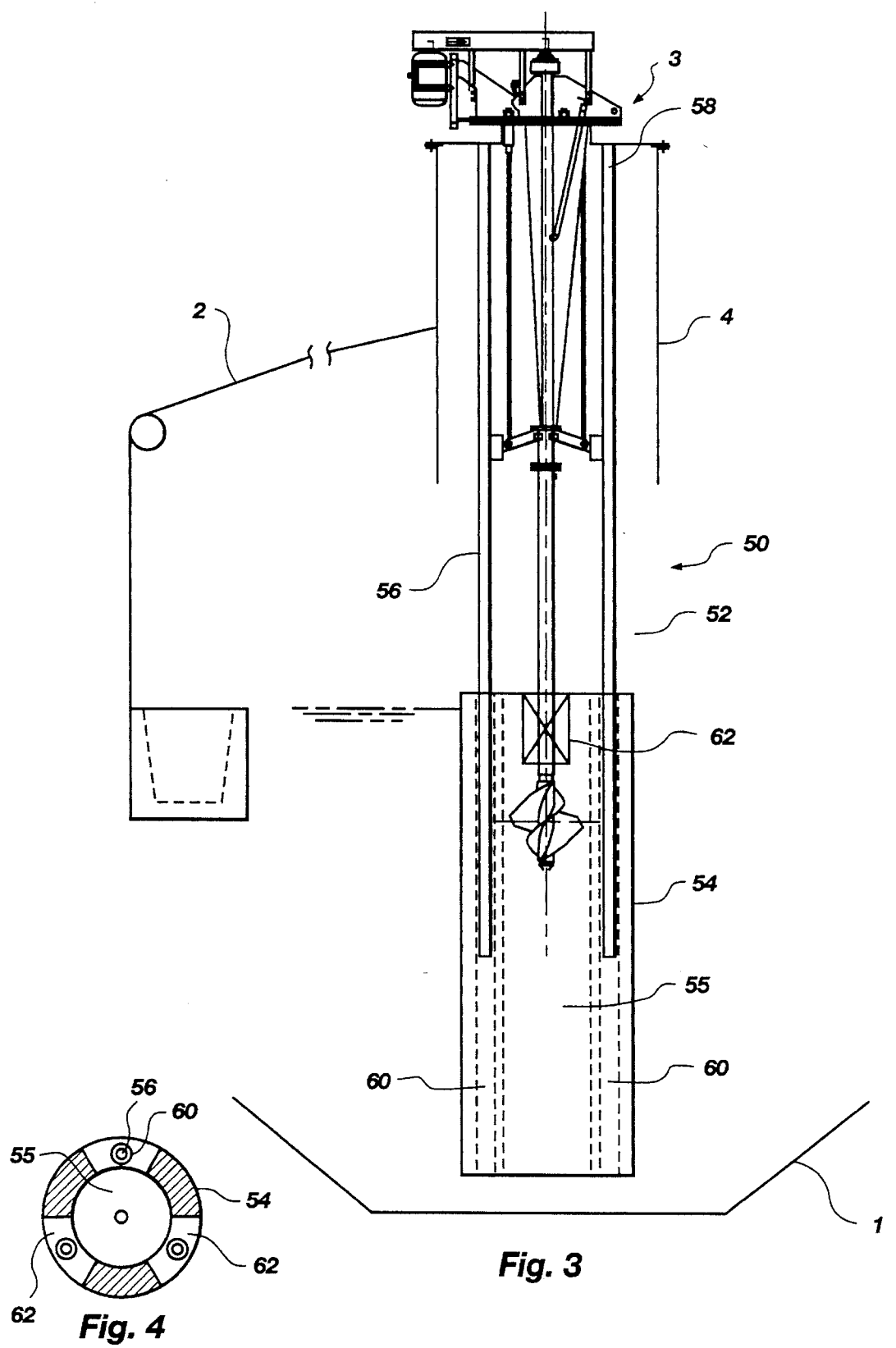
FIG. 3 is a side view of a second embodiment of the present invention in a digester at its lower liquid level.
FIG. 4 is a top view of the second embodiment of the present invention shown in FIG. 3.

Referring to drawing FIG. 3, a second embodiment 50 of the float tube assembly of the present invention is shown.

The float tube assembly 50 comprises float tube guide assembly 52 and floating housing 54.

The float tube guide assembly 52 comprises a plurality of individual guide tubes 56 which are typically elongated cylindrical tubes having their upper ends 58 secured to a portion of the mixing apparatus 3. Each guide tube 56 may be any suitable length depending upon the size of the digester 1. The diameter of each tube 56 may be of any convenient size depending on the size of the floating housing 54, the annular wall thickness of floating housing 54 and the desired rigidity of the structure. The lower ends of each guide tube 56 may be sealed, if desired.

The floating housing 54 comprises an elongated annular cylindrical housing having a bore 55 therethrough, a plurality of longitudinal apertures 60 and one or more notches 62 formed in the upper end thereof. If desired, the lower end of each aperture 60 may be sealed. The interior of the floating housing 54 may be filled with any desirable floatation means, such as closed cell foam and other means discussed hereinbefore to provide the necessary floatation of the floating housing 54 within digester 1. As shown, the floating housing 54 is in its lowermost position with respect to the digester 1 and mixing apparatus 3 therein.

Referring to drawing FIG. 4, the guide tubes 56 and floating housing 54 are shown from the top. As illustrated, each guide tube 56 is received in longitudinal aperture 60 in the floating housing 54 thereby allowing the floating housing 54 to move longitudinally with respect to the guide tubes 56.

Figure 5:
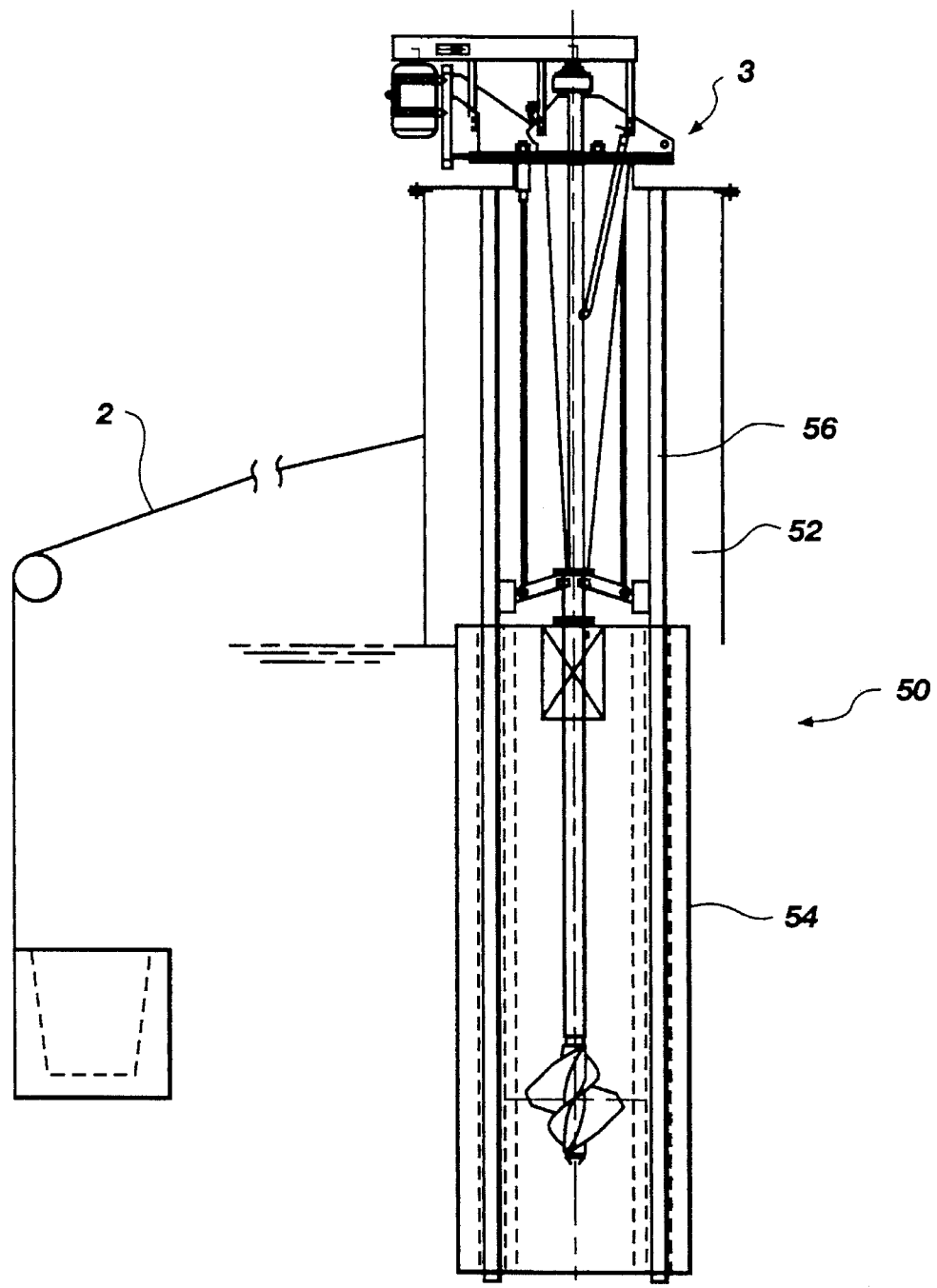
FIG. 5 is a side view of the second embodiment of the present invention shown in FIG. 3 in a digester at its upper liquid level.

Referring to drawing FIG. 5, the float tube assembly 50 is shown in its uppermost position within the digester 1 and mixing apparatus 3 therein.

If desired, the guide tubes 56 may extend beyond the floating housing 54 when it is in its lowest position with each tube 56 having a horizontal flat plate or other means secured on the bottom thereof to prevent the floating housing 54 from disengaging the guide tubes 56.

Figure 6:
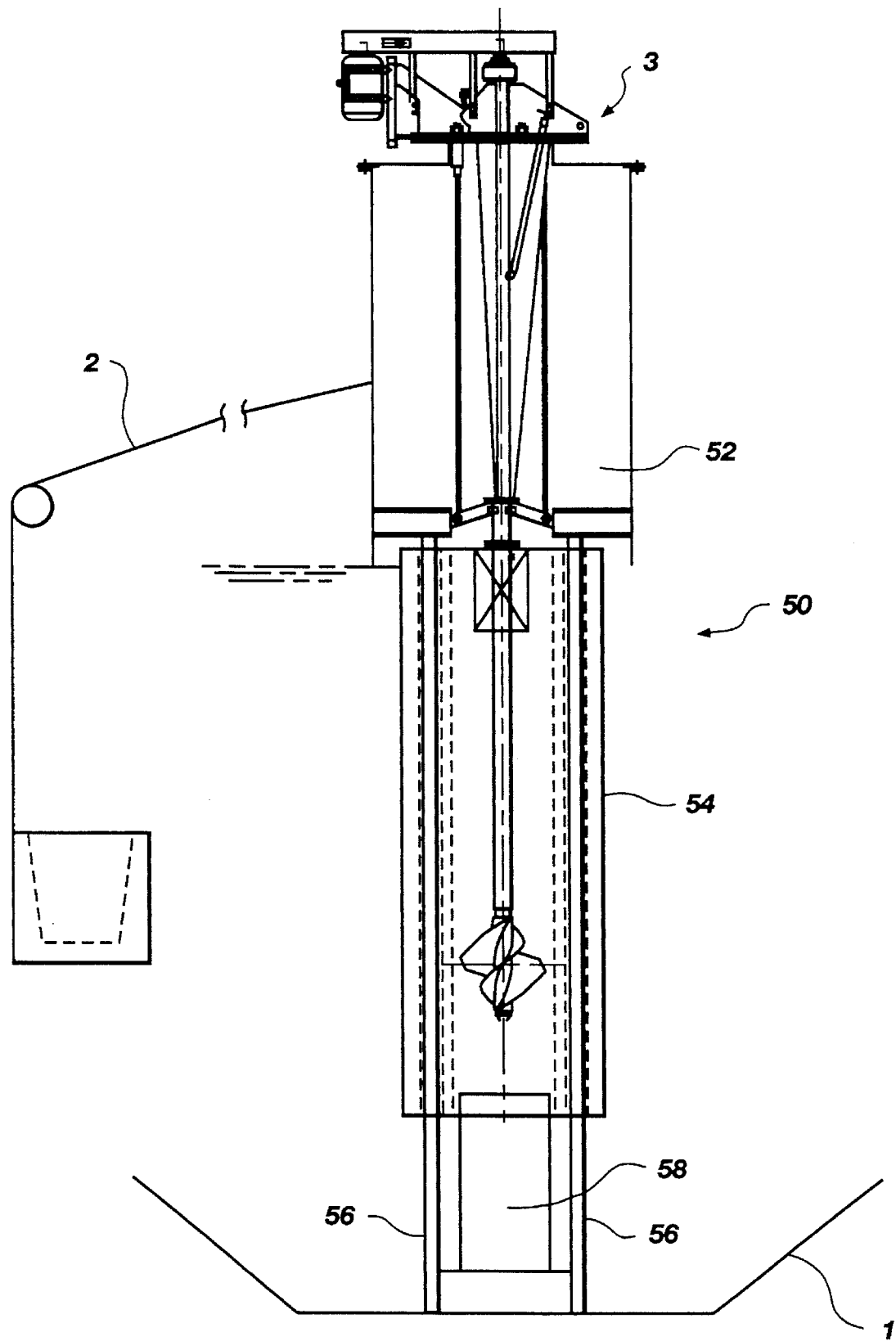
FIG. 6 is a side view of a third embodiment of the present invention in a digester.

Referring to drawing FIG. 6, a third embodiment 50 of the float tube assembly is shown. In the embodiment 50, the guide tubes 56 are secured to the bottom of a digester 1, rather than the mixer. In this manner the floating housing 54 may float with respect to the guide tubes 56. Secured by any suitable means to the lower portions of guide tubes 56 is a fixed housing 58 which serves to direct mixed liquids, scum and foam downwardly into the sludge. The fixed housing 58 has sufficient length to have a portion thereof engaging the bore of floating housing 54 when floating tube 54 is in its highest position within digester 1. If desired, a seal such as discussed hereinbefore may be included between fixed housing 58 and float housing 54.

Figure 7:
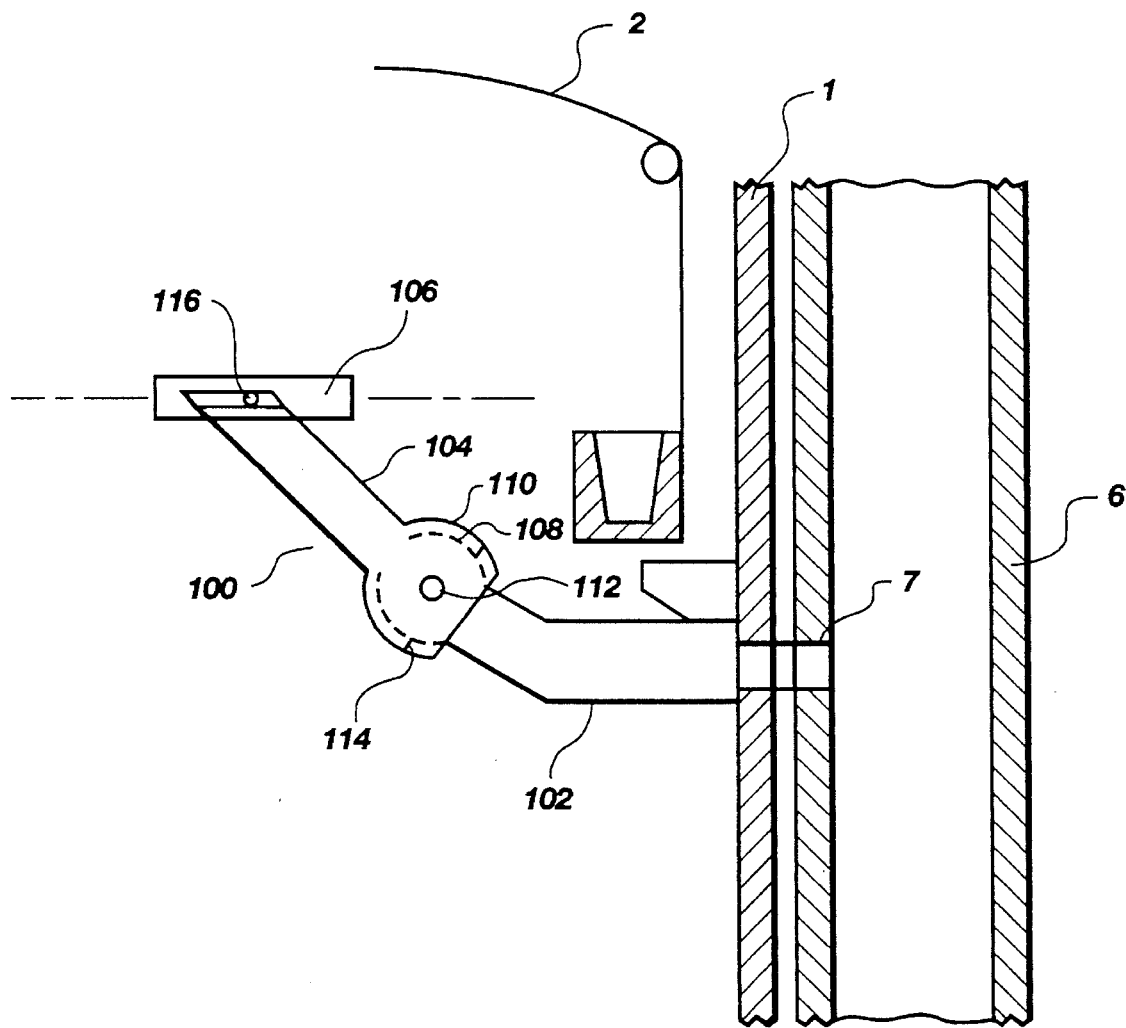
FIG. 7 is a side view of a fourth embodiment of the present invention in a digester having an external mixing chamber.

Referring to drawing FIG. 7, a fourth embodiment 100 of the float tube assembly is shown. The digester 1 has a floating cover 2 thereon. Rather than contain an internal mixing apparatus mounted on or through the cover 2, the digester 1 contains one or more mixing apparatus (not shown) installed in mixing chambers 6 which are located on the exterior of the digester 1. The mixing chambers 6 are in fluid communication with the digester 1 via conduits 7 and float tube assembly 100 connected thereto.

The float tube assembly 100 comprises fixed inner housing 102, floating housing 104 and float 106.

The fixed inner housing 102 comprises an elongated annular cylindrical member having one end thereof in fluid communication with conduit 7, 215 and the other end thereof, having the male portion 108 of a barrel receptacle connection formed thereon. The shape of the male portion of the barrel receptacle may be of any desired profile, such as rectangular. The length of the fixed inner housing 102 may be as desired depending upon the size of the digester 1 and the fluids therein.

The floating housing 104 comprises an elongated annular cylindrical member having, on one end thereof, the female portion 110 of a barrel type receptacle and, the other end thereof, being open. The female portion 110 of the barrel mates with male portion 108 of fixed housing 102. The female portion 110 is free to rotate with respect to male portion 108 via cylindrical tube 112 extending therethrough. A seal 114 may be included between fixed housing 102 and floating housing 104, if desired, to keep debris from becoming lodged therebetween in the male portion 108 and female portion 110. The seal 114 may be of any suitable type as discussed hereinbefore to scrape debris from the housing 102, 104 but need not be fluid fight.

The float 106 may be of any suitable type, such as rectangular pontoons filled with closed cell foam or other means discussed hereinbefore, one on each side of the end of the floating housing 104. The float 106 is movably connected to the end of the floating housing 104 via cylindrical tube 116 extending therethrough. In that manner, the end of the floating housing 104 may rise and fall with respect to fixed housing 102 via female portion 110 and male portion 108, respectively, as the fluids levels within the digester rise and fall.

Alternatively, the floating housing 104 may be a large flexible hose or pipe connected to the fixed housing 102 by a suitable flexible bellows or the like, desired, thereby eliminating the necessity of fabricating a barrel type receptacle.

It will be obvious to those of ordinary skill in the art that additions, deletions, changes and modifications to the present invention can be made which will fall within the scope of the present invention.

Although the float robe assemblies of the present invention have been described with respect to a digester, the float robe assemblies could be used with a mixer in any type biological reactor apparatus where mixing is needed.

It can be easily seen that the float robe assemblies of the present invention offer the advantage that the mixing apparatus may be supplied with liquids from the digester or biological reactor throughout a greater range of operating fluid liquids levels.

What is claimed is:

1. In combination, a float tube assembly and a mixing apparatus installed in a digester having liquids therein during waste disposal processes, said digester including a floating cover to which said mixing apparatus is secured, said mixing apparatus having a portion thereof extending into said liquids and said float tube assembly during said waste disposal processes, said float tube assembly comprising:

a plurality of vertically extending tubes, each tube having one end thereof connected to a portion of said mixing apparatus and having a portion thereof extending into said liquids in said digester;

an annular floating tube having a plurality of apertures extending longitudinally throughout the length of the wall thereof and having a bore therethrough into which said mixing apparatus portion extends, the annular floating tube apertures slidably reciprocally engaging portions of the plurality of vertically extending tubes to permit said annular floating tube to move vertically independently of said mixing apparatus, the annular floating tube having a buoyant force allowing the annular floating tube to float in said liquids in said digester.

2. The combination of claim 1, wherein each tube of the plurality of tubes has a portion thereof engaging at least a portion of an aperture of the plurality of apertures extending longitudinally throughout the length of the wall of the annular floating tube.

3. The combination of claim 1, wherein the annular floating tube has an aperture in the upper end thereof to allow said liquids within said digester to flow into the bore of the annular floating tube.

4. In combination, a float tube assembly and a mixing apparatus installed in a digester having liquids therein during waste disposal processes, said mixing apparatus having a portion thereof extending into said liquids during said waste disposal processes, said float tube assembly comprising:

a plurality of vertically extending tubes, each tube having one end thereof connected to said digester and having a portion thereof extending into said liquids in said digester;

an annular floating tube having a plurality of apertures extending longitudinally throughout the length of the wall thereof and having a bore therethrough into which said mixing apparatus portion extends, the annular floating tube apertures slidably reciprocally engaging portions of the plurality of vertically extending tubes to permit said annular floating tube to move vertically independently of said mixing apparatus, the annular floating tube having a buoyant force allowing the annular floating tube to float in said liquids in said digester.

5. The combination of claim 4, wherein each tube of the plurality of tubes has a portion thereof engaging at least a portion of an aperture of the plurality of apertures extending longitudinally throughout the length of the wall of the annular floating tube.

6. The combination of claim 5, wherein the annular floating tube has an aperture in the upper end thereof to allow said liquids within said digester to flow into the bore of the annular floating tube.

7. In combination, a float tube assembly and a mixing apparatus installed in a digester having liquids therein during waste disposal processes, said digester including a floating cover to which said mixing apparatus is secured, said mixing apparatus having a portion thereof extending into said liquids and said float tube assembly during said waste disposal processes, said float tube assembly comprising:

a vertically extending float guide structure having one end thereof connected to a portion of said mixing apparatus and having a portion thereof extending into said liquids in said digester;

an annular floating tube having a bore therethrough into which said mixing apparatus portion extends, said annular floating tube slidably reciprocally engaging a portion of the float guide structure to permit said annular floating tube to move vertically independently of said mixing apparatus, the annular floating tube having a buoyant force allowing the annular floating tube to float in said liquids in said digester.

8. The combination of claim 7, wherein the annular floating tube has an aperture in the upper end thereof to allow said liquids within said digester to flow into the bore of the annular floating tube.

9. In combination, a float tube assembly and a mixing apparatus installed in a digester having liquids therein during waste disposal processes, said mixing apparatus having a portion thereof extending into said liquids during said waste disposal processes, said float tube assembly comprising:

a vertically extending float guide structure having one end thereof connected to said digester and having a portion thereof extending into said liquids in said digester;

an annular floating tube having a bore therethrough into which said mixing apparatus portion extends, said annular floating tube slidably reciprocally engaging a portion of the float guide structure to permit said annular floating tube to move vertically independently of said mixing apparatus, the annular floating tube having a buoyant force allowing the annular floating tube to float in said liquids in said digester.

10. The combination of claim 9, wherein the annular floating tube has an aperture in the upper end thereof to allow said liquids within said digester to flow into the bore of the annular floating tube.

* * * * *

UNITED STATES PATENT AND TRADEMARK OFFICE
CERTIFICATE OF CORRECTION

PATENT NO. : 5,525,216
DATED : June 11, 1996
INVENTOR(S) : Matasovic

It is certified that error appears in the above-indentified patent and that said Letters Patent is hereby corrected as shown below:

In column 1, line 11, change "actor" to --reactor--;
In column 2, line 27, change "fast" to --first--;
In column 2, line 50, change "fight" to --tight--;
In column 2, line 53, change "faced" to --fixed--;
In column 2, line 56, change the comma after "thereof" to a period;
In column 3, line 22, change "28'" to --28--;
In column 4, line 8, after "floating" (second occurrence) change "tube" to --housing--;
In column 4, line 24, after "7," delete "215";
In column 4, line 25, delete the comma after "thereof";
In column 4, line 56, after "like," insert --if--;
In column 4, lines 64 and 66, change "robe" to --tube--; and
In column 5, line 1, change "robe" to --tube--.

Signed and Sealed this

Twenty-sixth Day of November 1996

Attest:

BRUCE LEHMAN

*Attesting Officer*     *Commissioner of Patents and Trademarks*